US00PP37263P2

(12) United States Plant Patent
Scheffers

(10) Patent No.: US PP37,263 P2
(45) Date of Patent: Feb. 10, 2026

(54) ***CEROPEGIA* PLANT NAMED 'LUUK'**

(50) Latin Name: ***Ceropegia linearis* E. Mey. subsp. *woodii* (Schltr.) H. Huber syn. *Ceropegia woodii***
Varietal Denomination: LUUK

(71) Applicant: Aad Scheffers, Honselersdijk (NL)

(72) Inventor: Aad Scheffers, Honselersdijk (NL)

( * ) Notice: Subject to any disclaimer, the term of this patent is extended or adjusted under 35 U.S.C. 154(b) by 0 days.

(21) Appl. No.: 18/831,575

(22) Filed: Apr. 30, 2025

(51) Int. Cl.
*A01H 5/12* (2018.01)
*A01H 6/08* (2018.01)

(52) U.S. Cl.
USPC ..... Plt./373

(58) Field of Classification Search
USPC ..... Plt./373, 226, 263.1
CPC ... A01H 5/12; A01H 5/00; A01H 6/08; A01H 5/02
See application file for complete search history.

(56) References Cited

PUBLICATIONS

Cowell's Garden Center, retrieved on Aug. 13, 2025 at https://www.cowellsgc.co.uk/product/ceropegia-linearis-luuk-14cm-hanging-pot, 3 pp. (Year: 2025).*
PlantZAfrica *Ceropegia linearis subsp. woodii* 2019, retrieved on Aug. 13, 2025 at https://pza.sanbi.org/ceropegia-linearis-subsp-woodii, 13 pp. (Year: 2019).*
TikTok Oh So Floral, retrieved on Aug. 13, 2025 at https://www.tiktok.com/@ohsofloral_uk/video/7520997304820567298, one page. (Year: 2025).*

* cited by examiner

*Primary Examiner* — June Hwu
(74) *Attorney, Agent, or Firm* — Samuel R. McCoy, Jr.

(57) ABSTRACT

A new and distinct *Ceropegia woodii* plant named 'LUUK' which is characterized by a trailing habit, small narrowly cordate to near-deltoid foliage, borne on stems that are initially a near-pink general coloration and transform into yellow-green as the plant matures. This new variety also exhibits prominently variegated foliage that is green with irregularly arranged blotches of yellow-green on the adaxial laminar surface and narrowly outlined green margins. Occasionally some laminas will exhibit a homogenous cream white coloration. The new variety, 'LUUK', exhibits the stability of these characteristics from generation to generation.

2 Drawing Sheets

Latin name of the genus and species: The Latin name of the genus and species of the novel variety disclosed herein is *Ceropegia linearis* E. Mey. subsp. *woodii* (Schltr.) H. Huber syn. *Ceropegia woodii.*

Variety denomination: The inventive variety of *Ceropegia* disclosed herein has been given the variety denomination 'LUUK'.

BACKGROUND OF THE INVENTION

Parentage: The new plant originated as a spontaneous, partial-plant, branch mutation. The mutation was discovered at a commercial greenhouse in Honselersdijk, The Netherlands, in April of 2022, growing amongst a plurality of cultivated *Ceropegia woodii* 'Iris' (not patented) plants. The mutation exhibited conspicuously variegated foliage and improved vigor, relative to the parent. From said mutated branch, a plurality of cuttings was harvested, rooted, and grown to a mature size in order to evaluate stability and uniqueness of the characteristics first observed. Of these new plants, most exhibited at least some degree of reversion in the foliage color, back to that of the parental phenotype. All plants that showed reversion were discarded, while stem cuttings were harvested from those plants that retained the unique variegation. This process was repeated twelve times until all progeny from an individual cutting-grown plant retained the characteristics first observed in April of 2022. After four successful propagation cycles of the stable characteristics, this specific ortet was selected for commercialization and given the name, 'LUUK'.

Asexual Reproduction: Asexual reproduction of the new cultivar 'LUUK', by way of softwood stem cuttings, in Honselersdijk, The Netherlands. Through four subsequent generations, the unique features of this cultivar have proven to be stable and true to type.

SUMMARY OF THE INVENTION

The cultivar 'LUUK' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LUUK'. These characteristics in combination distinguish 'LUUK' as a new and distinct *Ceropegia* cultivar:

1. *Ceropegia* 'LUUK' exhibits relatively small, narrowly cordate to near-deltoid foliage; and
2. *Ceropegia* 'LUUK' exhibits prominently variegated foliage that is green with the veins and areas of the laminar surface immediately adjacent to veins colored with a light yellow-green; and
3. *Ceropegia* 'LUUK' exhibits foliage that is irregularly and narrowly margined with a green coloration; and 4. *Ceropegia* 'LUUK' exhibits a trailing branching habit with stems that are initially purple to greyed-red which transform into yellow-green as the plant matures.

BOTANICAL DESCRIPTION OF THE PLANT

Figure 1:
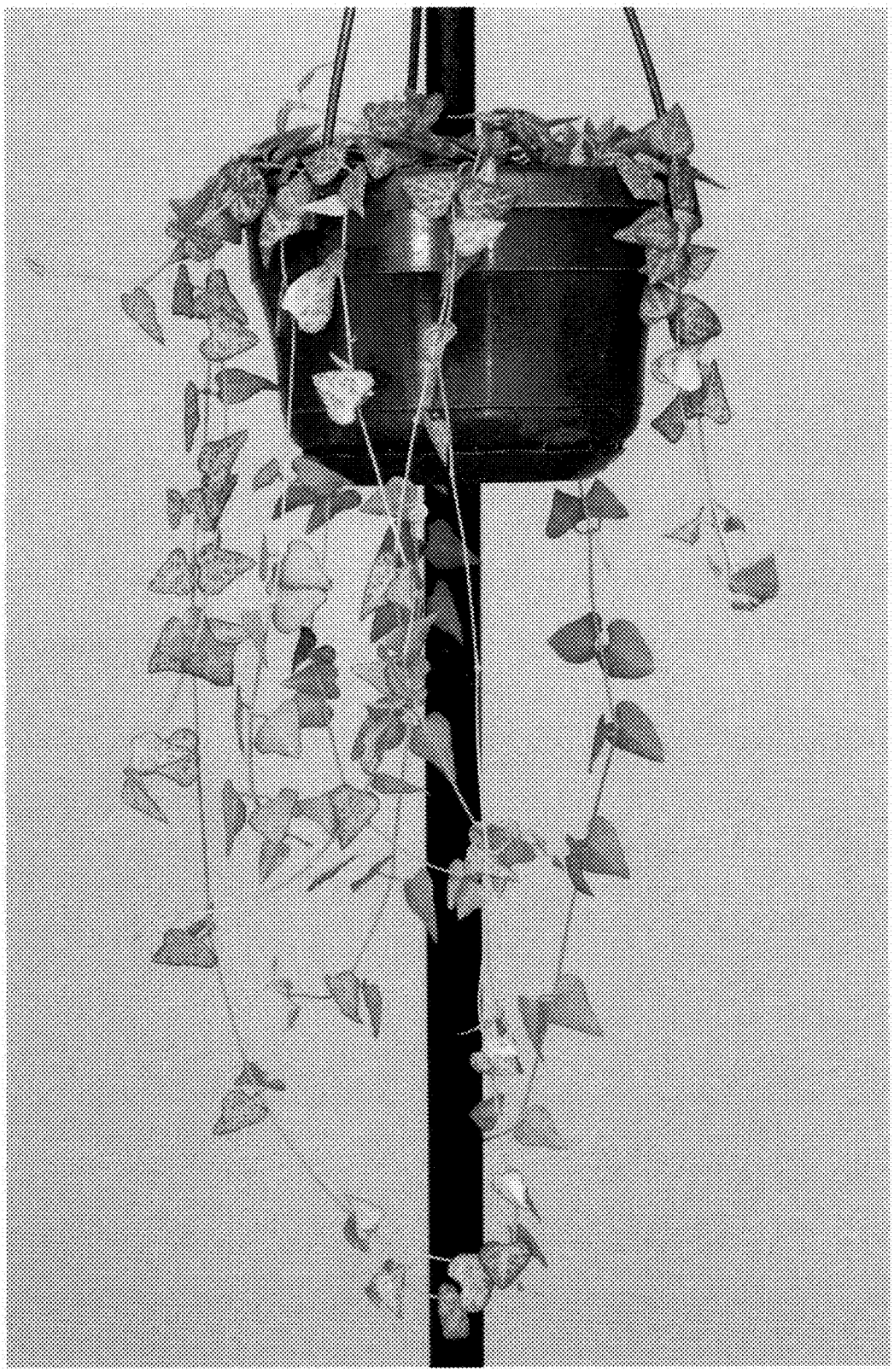
FIG. 1 illustrates, as nearly true as it is reasonably possible to make the same in color photographs of this type, an exemplary 12-month-old 'LUUK' plant in a 14 cm nursery pot, grown in a greenhouse in Honselersdijk, The Netherlands.
Figure 2:
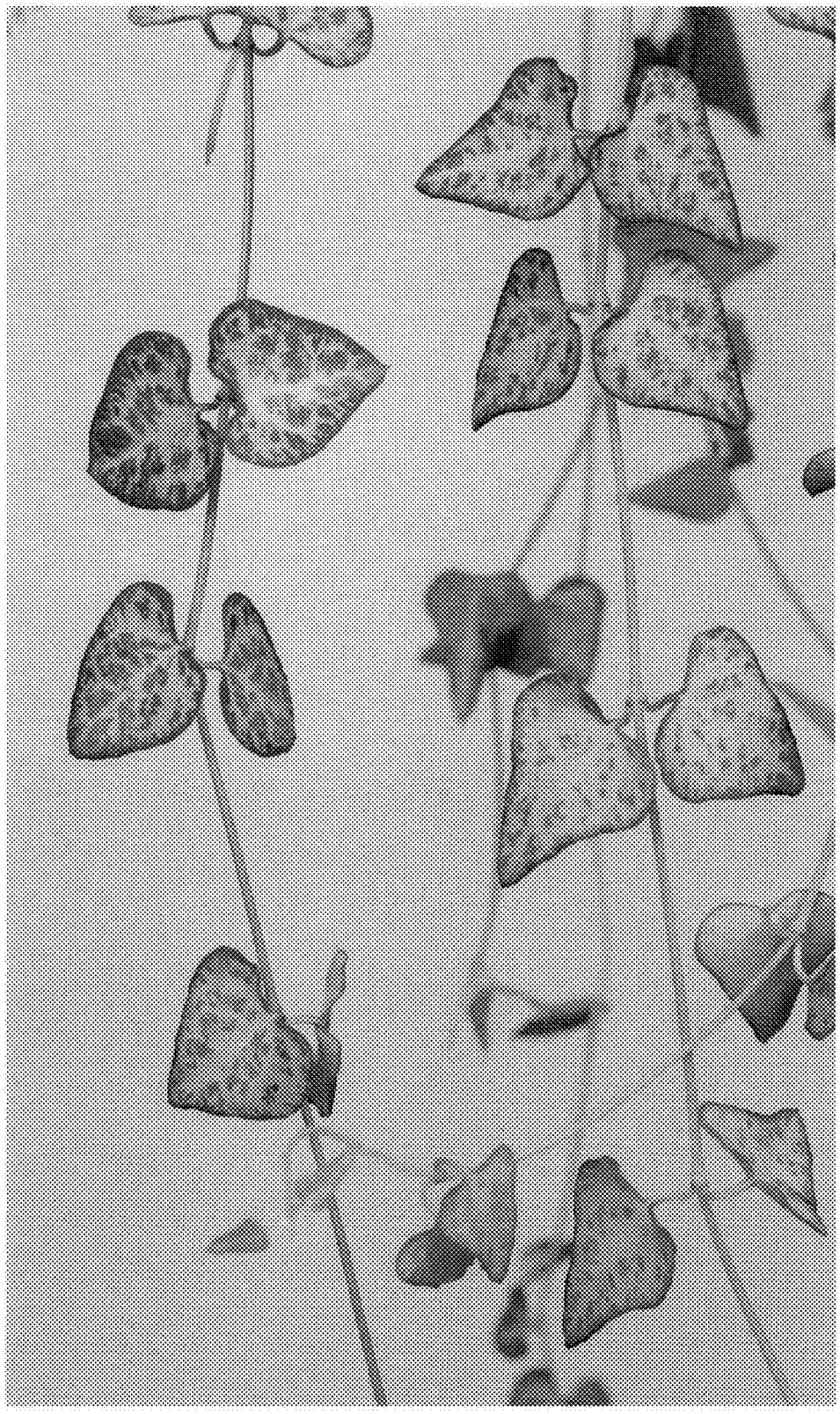
FIG. 2 illustrates, as nearly true as it is reasonably possible to make the same in color photographs of this type, the progression of foliar variegation through maturation of 'LUUK'.

The following observations and measurements were made in February of 2025 and describe a 12-month-old 'LUUK' plant grown in a 14 cm nursery pot at a commercial greenhouse in Honselersdijk, The Netherlands. Plants were grown using conventional greenhouse production protocols for *Ceropegia* which consisted of growing under 50 percent shade with regular overhead irrigation and fertilizer applications as needed. Pesticides were used to control thrips, but no pest or disease control measures were otherwise utilized in production. No photoperiodic treatments or artificial light was given to the plants.

Those skilled in the art will appreciate that certain characteristics will vary with older or, conversely, with younger plants. 'LUUK' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, Sixth Edition.

A botanical description of 'LUUK' and comparisons with the parent and most similar commercial variety of *Ceropegia* are provided below.

Plant description:

*Growth habit.*—Evergreen trailing vine perennial.

*Average height from base to top of foliage.*—In a hanging basket, the plant is 40.0 cm from the top of the foliar plane to the apex of the lowest trailing stem.

*Average width.*—23.9 cm.

*Propagation method.*—Softwood stem cuttings; rooting is initiated in approximately 14 days, when grown in a greenhouse with an ambient average temperature of 20 degrees Celsius.

*Time to produce a finished plant.*—Approximately 5 months are required to produce a fully rooted and marketable 14 cm plant when grown under greenhouse conditions.

*Environmental tolerances.*—Adapt to at least USDA Zones 11 through 13; low to moderate tolerance to rain; low tolerance to wind; moderate tolerance to drought.

Root system:

*General.*—Caudices at the base of main stems, at and slightly below the soil level, give rise to a moderately dense network of fleshy roots.

*Distribution in the soil profile.*—Roots are relatively shallow.

*Texture.*—Fleshy; no root hairs present.

Stem:

*Branching habit.*—Basally branching main stem; lateral branching forms when pruning methods are applied.

*Quantity of main stems per plant.*—17.

*Aspect.*—Rounded.

*Length of main stems.*—35.7 cm, on average.

*Diameter of main stems.*—0.1 cm, on average.

*Internode length on main stems.*—4.0 cm, on average.

*Attitude.*—Prostrate; strongly weeping, when grown in a hanging basket.

*Strength.*—Moderately strong.

*Texture and luster.*—Glabrous and slightly glossy.

*Color, juvenile.*—Purple to greyed-red, nearest to a mixture of RHS 75C and 182D.

*Color, mature.*—Yellow-green, nearest to RHS 145C.

*Color at internodes.*—Yellow-green, nearest to RHS 145C.

Foliage:

*Arrangement.*—Opposite.

*Division.*—Simple.

*Attachment.*—Petiolate.

*Quantity.*—Average of 18 leaves per branch.

*Lamina.*—Dimensions — 2.2 cm long and 1.8 cm wide, on average. Shape — Narrow cordate to near deltoid. Aspect — Flat. Apex — Acute. Base — Cordate to shallowly truncate. Margin — Entire; occasionally very slightly undulate. Pubescence, texture and luster of adaxial surface — Glabrous, smooth, and matte. Pubescence, texture and luster of abaxial surface — Glabrous, smooth, and matte. Color — Juvenile foliage, adaxial surface — Yellow-green, nearest to RHS 144A, and blotched with a slightly darker yellow-green, nearest to RHS 145B; irregularly and narrowly margined green, nearest to RHS 143B. Occasionally the entire laminar surface may be white, nearest to RHS 155C, with greyed-white RHS 155A blotches. Juvenile foliage, abaxial surface — Yellow-green, nearest to RHS 144C. Occasionally the entire lamina may be homogenously white, nearest to RHS 155C. Mature foliage, adaxial surface — Green, nearest to RHS 143B, and very densely marbled with blotches of yellow-green, nearest to RHS 147D; irregularly and narrowly margined green, nearest to RHS 143A. Occasionally the entire laminar surface may be white, nearest to RHS 155C, with greyed-white RHS 155A blotches, as well as randomly placed blotches of green, RHS 143B. Mature foliage, abaxial surface — Green, nearest to a blend of RHS 138B and 138C, irregularly and narrowly margined green, nearest to RHS 143A. Occasionally the entire lamina may be homogenously white, nearest to RHS 155C. Venation — Pattern — Pinnate. Venation color, adaxial surface of mature foliage — Yellow-green, nearest to RHS 147D. Venation color, abaxial surface of mature foliage — Yellow-green, nearest to a blend of RHS 146C and 146D.

*Petiole*.—Length — 0.6 cm. Width — 0.1 cm. Texture — Smooth and glabrous. Luster — Matte. Strength — Moderately strong. Color, adaxial surface — Yellow-green to greyed-green, nearest to a blend of 148C and 195B. Color, abaxial surface — Greyed-green, nearest to RHS 195B.

Inflorescence:

*Inflorescence type*.—Cyme.

*Natural flowering season*.—Late June through early August in the Netherlands.

*Dimensions*.—Approximately 3.1 cm long, including peduncle, and 5.7 cm wide.

*Quantity of open flowers and buds per inflorescence*.—4.

*Attitude*.—Pendulous.

*Peduncles*.—Length — Average of 1.0 cm. Diameter — Average of 0.6 cm. Attitude — Outward. Strength — Moderately strong. Texture and luster — Smooth, glabrous and matte. Color — Greyed-green, nearest to RHS 197B.

Bud:

*Shape*.—Oblong.

*Dimensions*.—5.5 mm long and 1.5 mm in diameter.

*Color*.—Immature sepals and corolla tube are yellow-green, RHS 150D; immature petals are greyed-orange, nearest to RHS N170C.

*Texture*.—Smooth and glabrous.

*Luster*.—Slightly glossy.

Flower:

*Form*.—Tubulate; the corolla is fused into a floral tube, swollen at the base, with free petal lobes, distally, which are fused at their apices.

*Attitude*.—Outward to upright.

*Lastingness*.—Approximately 14 days.

*Persistence*.—Not persistent; self-cleaning.

*Fragrance*.—Not fragrant.

*Flower depth*.—2.1 cm.

*Flower diameter*.—0.35 cm.

*Diameter of floral throat*.—0.3 cm.

*Floral throat texture*.—Glabrous; smooth.

*Diameter of floral tube*.—0.25 cm at the distal end; at the base, where the floral tube is swollen, the diameter is 0.4 cm.

*Length of floral tube*.—1.6 cm.

*Floral tube texture*.—Glabrous; smooth.

*Pedicels*.—Attitude — Outward, at an average angle of 30 degrees to the peduncle. Dimensions — 5.5 mm long and 0.5 mm in diameter. Strength — Moderately strong. Texture and luster — Smooth, glabrous, and matte. Color — Greyed-green, nearest to RHS 197C.

*Petals*.—Quantity of Petals — 5. Arrangement — The petals are fused into a long floral tube, with a single whorl of free petal lobes, distally. Attitude of petal lobes — Curved inward, particularly at and near the apex, and fused to all other petal lobes at the apex, forming a "cage" over the floral throat. Shape of petal lobes — Narrowly spatulate. Aspect of petal lobes — Strongly carinate and irregularly twisted. Dimensions, free portion of petals — 0.55 cm long and 0.2 cm wide. Apex — Obtuse yet appearing as near-acute used. Base — Truncate; fused at the base. Margin — Entire and ciliate; hairs are 0.25 mm in length and are colored with a mixture of greyed-purple and black, nearest to RHS 186B and 202A. Petal lobes are not undulated. Pubescence, texture and luster of outer surface — Smooth, glabrous, and slightly glossy. Pubescence, texture and luster of inner surface — Smooth, glabrous and matte. Corolla tube color when opening, inner surface — Swollen portion of the floral tube near the base of the corolla is greyed-purple, nearest to RHS 186D; the narrower portion of the floral tube is purple, nearest to RHS N77A. No visible venation. Corolla tube color when opening, outer surface — Swollen portion of the floral tube near the base of the corolla is greyed-green, RHS 198D; narrower portion of the floral tube is a mixture of purple and greyed-red, nearest to RHS 75C and 182D. No visible venation. Petal lobe color when opening, inner surface — Nearest to a mixture of greyed-purple and black, RHS N186A and 202A. No visible venation. Petal lobe color when opening, outer surface — Nearest to a mixture of greyed-purple and black, RHS N186A and 202A. No visible venation. Corolla tube color when fully open, inner surface — Swollen portion of the floral tube near the base of the corolla is greyed-green, RHS 198D; narrower portion of the floral tube is a mixture of purple and greyed-red, nearest to RHS 75C and 182D. No visible venation. Corolla tube color when fully open, outer surface — Swollen portion of the floral tube near the base of the corolla is greyed-purple, nearest to RHS 186C; narrower portion of the floral tube is purple, nearest to RHS N77A. No visible venation. Petal lobe color when fully opened, inner surface — Greyed-purple, nearest to RHS N186A. No visible venation. Petal lobe color when fully opened, outer surface — Greyed-purple, RHS N186A. No visible venation. Floral throat color — Nearest to a mixture of purple and greyed-red, RHS 75C and 182D. No visible venation. Corolla tube color when faded, inner surface — Colors do not fade. No visible venation. Corolla tube color when faded, outer surface — Swollen portion of the floral tube near the base of the corolla is greyed-green, nearest to RHS 198D; narrower portion of the floral tube is greyed-red, nearest to RHS 182D yet lighter. No visible venation. Petal lobe color when faded, inner surface — Colors do not fade. No visible venation. Petal lobe color when faded, outer surface — Nearest to a mixture of greyed-purple and black, RHS N186A and 202A. No visible venation.

*Calyx*.—Shape — Rotate; single whorl of sepals. Dimensions — 0.4 cm in diameter and 0.2 cm deep. Sepals — Arrangement — Sepals are rotate and fused at the base. Quantity — 5. Shape — Linear. Dimensions — 2.0 mm long and 0.35 mm wide. Apex — Narrow acuminate. Base — Cuneate; fused. Margin — Entire; not undulated. Pubescence, texture and luster, upper surface — Smooth; glabrous; matte. Pubescence, texture and luster, lower surface — Smooth; glabrous; matte. Color when opening, inner surface — White, nearest to RHS N155A. Color when opening, outer surface — White, nearest to RHS N155B. Color when fully opened, inner surface — White, nearest to RHS N155A. Color when fully opened, outer surface — White, nearest to RHS N155B.

Reproductive organs:

*General description*.—Stamens and pistils are adnated into a gynostegium.

*Dimensions*.—Approximately 1.1 mm long and 1.0 mm wide.

*Color*.—Reduced filaments are a combination of white and greyed-yellow, nearest to RHS N155A and 160D; reduced anthers are greyed-orange, nearest to RHS 164C; reduced pistils are white, nearest to RHS N155A.

*Pollen, amount*.—Pollen is sparse and massed into globular pollinia at the base of the gynostegium.

*Pollinia color*.—Greyed-orange, nearest to RHS 164A.

*Ovary color*.—Greyed-purple, nearest to RHS N186B.

Seed and fruit: Seeds and fruit have not been observed to date.

COMPARISONS WITH THE PARENT PLANT

Plants of the new cultivar 'LUUK' differ from the parent, *Ceropegia linearis* 'Iris' (not patented), by the characteristics described in Table 1.

TABLE 1

Comparison Between 'LUUK' and 'Iris'.

| Characteristic | 'LUUK' | 'Iris' |
|---|---|---|
| Coloration of stems in juvenile stage. | Purple to greyed-red, appearing pink. | Light green, with an overtone of brown. |
| Coloration of stems in mature growth. | Yellow-green. | Light green, with an overtone of brown. |
| Expression of foliar variegation and coloration on the adaxial surface of mature foliage. | A lighter suffusion of variegated green and yellow-green that is less prominent than 'Iris'. | A darker suffusion of variegated green that is more prominent than 'LUUK'. |

TABLE 1-continued

Comparison Between 'LUUK' and 'Iris'.

| Characteristic | 'LUUK' | 'Iris' |
|---|---|---|
| Expression of foliar variegation and coloration on the abaxial surface of mature foliage. | Predominantly colored green, with a prominent irregularly outlined dark green margin. | Lighter than 'LUUK', closer to greyed-green or white with no outline along the margin. |

COMPARISON WITH THE MOST SIMILAR *CEROPEGIA* CULTIVAR KNOWN TO THE INVENTOR

Plants of the new cultivar 'LUUK' differ from the commercial variety, *Ceropegia* 'Merel' (U.S. Plant Pat. No. 35,793), in the following characteristics described in Table 2 below.

TABLE 2

Comparison Between 'LUUK' and 'Merel'

| Characteristic | 'LUUK' | 'Merel' |
|---|---|---|
| Plant Size. | Smaller than 'Merel' on average, 40 cm in length from the top of the foliar plant to the apex of the lowest trailing stem. | Larger than 'LUUK' on average, 97 cm in length from the top of floral plane to the apex of the lowest trailing stem. |
| Expression of foliar variegation and coloration on the adaxial surface of mature foliage. | Lighter green than 'Merel', very densely marbled with blotches of yellow-green and narrowly margined green. | Darker green than 'LUUK', moderately dense with blotches of greyed-green and broadly margined white. |

That which is claimed is:

1. A new and distinct *Ceropegia woodii* plant named 'LUUK', substantially as described and illustrated herein.

* * * * *